(12) United States Patent
Willemstyn et al.

(10) Patent No.: US 7,950,700 B2
(45) Date of Patent: May 31, 2011

(54) CONNECTOR ASSEMBLY FOR STERILE CONNECTORS

(75) Inventors: Benjamin Willemstyn, Little Silver, NJ (US); Timothy Korwan, Reading, MA (US)

(73) Assignee: PAW BioScience Products, Inc., Eatontown, NJ (US)

( * ) Notice: Subject to any disclaimer, the term of this patent is extended or adjusted under 35 U.S.C. 154(b) by 203 days.

(21) Appl. No.: 12/261,539

(22) Filed: Oct. 30, 2008

(65) Prior Publication Data
US 2009/0230633 A1 Sep. 17, 2009

Related U.S. Application Data

(60) Provisional application No. 61/069,337, filed on Mar. 13, 2008.

(51) Int. Cl.
*F16L 23/12* (2006.01)
*F16L 23/16* (2006.01)

(52) U.S. Cl. ......... 285/364; 285/336; 285/379; 285/917

(58) Field of Classification Search .................. 285/336, 285/364, 379, 917, 365–368
See application file for complete search history.

(56) References Cited

U.S. PATENT DOCUMENTS

| | | | | |
|---|---|---|---|---|
| 3,141,685 A * | 7/1964 | Watts | ............................. | 285/93 |
| 3,839,778 A * | 10/1974 | Brothers | ......................... | 29/432 |
| 3,986,508 A | 10/1976 | Barrington | | |
| 4,168,852 A * | 9/1979 | Ahlstone | ....................... | 285/336 |
| 4,650,227 A * | 3/1987 | Babuder et al. | ............... | 285/379 |
| 5,011,196 A * | 4/1991 | Sabatier et al. | ............... | 285/367 |
| 5,050,914 A * | 9/1991 | Miyashita | ..................... | 285/336 |
| 5,145,219 A | 9/1992 | Babuder | | |
| 5,163,721 A * | 11/1992 | Babuder | ........................ | 285/328 |
| 5,466,018 A * | 11/1995 | Stobbart | .................... | 285/334.2 |
| 5,673,946 A * | 10/1997 | Barber et al. | ................. | 285/328 |
| 5,681,064 A * | 10/1997 | Aldridge et al. | ............. | 285/379 |
| 5,837,180 A * | 11/1998 | Linder et al. | ................. | 264/230 |
| 5,904,381 A * | 5/1999 | Ohmi et al. | .................... | 285/328 |
| 5,947,533 A * | 9/1999 | Fisher et al. | ................. | 285/350 |
| 5,997,045 A | 12/1999 | Boe et al. | | |
| 6,070,912 A * | 6/2000 | Latham | ........................... | 285/61 |
| 6,170,890 B1 * | 1/2001 | Ohmi et al. | .................... | 285/379 |
| 6,318,766 B1 * | 11/2001 | Babuder et al. | ............... | 285/328 |
| 6,454,316 B1 * | 9/2002 | Aaron, III | ..................... | 285/379 |
| 6,543,120 B2 * | 4/2003 | Aaron, III | ....................... | 29/451 |
| 7,581,764 B2 * | 9/2009 | Ishihara | ........................ | 285/336 |
| 2005/0212291 A1 * | 9/2005 | Edwards | ....................... | 285/364 |

OTHER PUBLICATIONS

The International Search Report and Written Opinion by the International Searching Authority, issued on May 5, 2009, in the PCT application No. PCT/US09/36970.

* cited by examiner

*Primary Examiner* — James M Hewitt

(57) ABSTRACT

A connector assembly and method of creating a connection is described. The connector assembly includes a connector fitting having at least one receiving component on an end of the connector fitting and a gasket having at least one appendage, where the at least one appendage of the gasket engages the at least one receiving component to create an at least temporary secured attachment of the gasket to the connector fitting end.

6 Claims, 7 Drawing Sheets

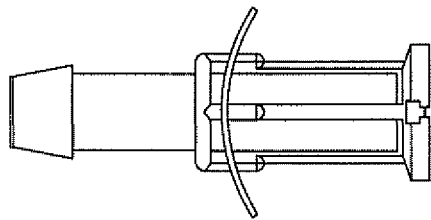
FIG. 2A  FIG. 2B  FIG. 2C
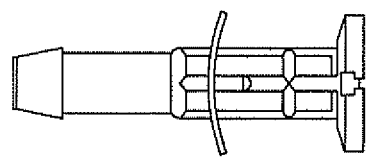
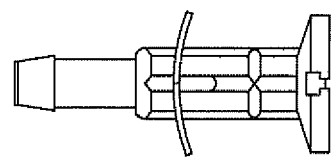
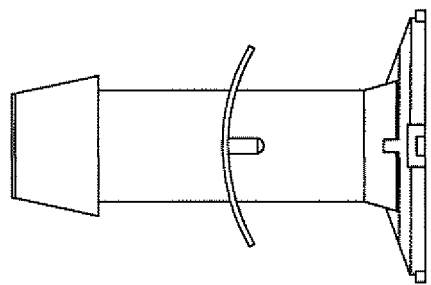
FIG. 2G
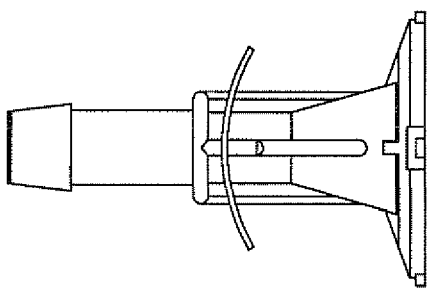
FIG. 2F
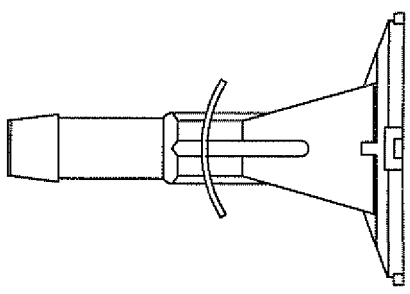
FIG. 2E
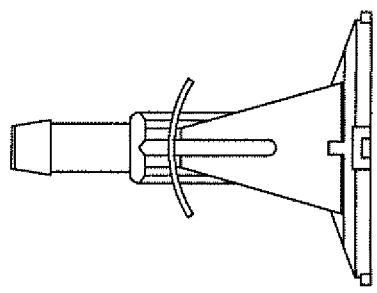
FIG. 2D

CONNECTOR ASSEMBLY FOR STERILE CONNECTORS

CROSS-REFERENCE TO RELATED APPLICATIONS

This application claims priority of U.S. Patent Application Ser. No. 61/069,337, filed Mar. 13, 2008, and is related to concurrently filed U.S. patent application Ser. No. 12/261,669, filed Oct. 30, 2008 and entitled CONNECTOR, GASKET AND METHOD OF ATTACHING THE SAME, the entire disclosures of which are incorporated by reference herein as if being set forth in their entireties.

FIELD OF THE INVENTION

The instant invention relates to the field of mechanical connectors, and in particular to connectors for use in fluid processing machinery or other applications used in a sterilized environment.

BACKGROUND OF THE INVENTION

Sanitary style flange fittings have been around for decades. For example, steel fittings are used widely in the dairy, pharmaceutical and biotechnology manufacturing industries.

These flange fittings typically have a hose barb (or nipple) on one side of the fitting for securing a fluid conduit, such as a flexible hose or tube. On the other side of the fitting, a flange to make a connection with another fluid conduit or piece of equipment is usually found. Using this design, the other fluid conduit or pieces of equipment would also need to have a matching flange in order to make the proper and effective connection.

However, the biotech and pharmalogical manufacturing industry has been moving away from these steel process systems and embracing what are commonly referred to as "single-use" systems, such as those made from disposable plastic parts and rubber tubing. These "single-use" systems are extremely varied, highly customized, and built to the end-users specifications for a broad range of manufacturing applications.

An example of a single-use sanitary flange fitting can be found in U.S. Pat. No. 6,893,428 ("the '428 patent"), the entire disclosure of which is incorporated by reference herein as if set forth in its entirety. As described in the '428 patent, an over-wrap bag is attached to a flange formed near the middle of the connector. The over-wrap bag maintains the sterility of the enclosed end of the connector. The other end of the connector is typically attached to a piece of tubing or conduit in communication with another larger bag, which has been rendered sterile collectively with the connector. Sterile fluids pumped into the bag, either though the connector itself, or through some other opening in the larger bag, will not be contaminated.

In use, the flange fitting is intended to make a connection with another flange fitting. To make the connection, a flat rubber gasket is placed between the face of the fittings. The gasket is designed to seat into the contours of the fitting face. The flange faces are pushed together (with the gasket in between) and a circular clamp is positioned around the circumference of flanges. The clamp has a swing-bolt that, once secured in place, permits the installer to tighten the two flange faces together and compress the gasket. Once connected, the two fittings form a fluid conduit relatively free from dead-spots and capable of handling substantially high pressures.

However, a drawback to these sterile flange fittings involves the installation of the gasket during connection. For example, the operator making the connection must hold the gasket in place, while at the same time align the flange faces and install the clamp around the fittings and gasket. This is a clumsy, cumbersome process at best and highly prone to contamination. Therefore, a need exists for a device, mechanism and method for readily attaching the gasket portion to the fittings of a connector while maintaining a sterile environment.

SUMMARY OF THE INVENTION

A gasket for attachment to the face of a connector fitting is described. The gasket includes a ring portion having a thickness suitable for creating a seal when compressed between two connector fitting ends, and at least one appendage pair, where each appendage of the at least one appendage pair includes an extension for engaging a reciprocally shaped receiving component on a connector fitting end to create an at least temporarily secured attachment of the gasket to the end of the connector fitting prior to creation of a seal between two connector fitting ends.

A connector assembly is also described. The connector assembly includes a connector fitting having at least one receiving component on an end of the connector fitting and a gasket having at least one appendage, where the at least one appendage of the gasket engages the at least one receiving component to create an at least temporary secured attachment of the gasket to the connector fitting end.

A method of creating a connection between two connector fittings is also described. The method includes the steps of engaging some or all of the appendages of a gasket with a reciprocally shaped receiving component of the connector fitting, such that the gasket is at least temporarily secured to the end of the connector fitting, sterilizing the gasket and connector fitting, placing the end of a second connector fitting adjacent to the gasket attached to the first connector fitting, such that the gasket is between the ends of the two connector fittings, and clamping the two connector fitting ends and gasket such that the gasket is compressed to form a seal and thereby create a connection between the two connector fittings.

BRIEF DESCRIPTION OF THE FIGURES

Understanding of the present invention will be facilitated by consideration of the following detailed description of the embodiments of the present invention taken in conjunction with the accompanying drawings, in which like numerals refer to like parts and in which:

FIG. 2A is a front view of an exemplary connector, according to an aspect of the present invention;

FIG. 2B is a front view of an exemplary connector, according to an aspect of the present invention;

FIG. 2C is a front view of an exemplary connector, according to an aspect of the present invention;

FIG. 2D is a front view of an exemplary connector, according to an aspect of the present invention;

FIG. 2E is a front view of an exemplary connector, according to an aspect of the present invention;

FIG. 2F is a front view of an exemplary connector, according to an aspect of the present invention;

FIG. 2G is a front view of an exemplary connector, according to an aspect of the present invention;

DETAILED DESCRIPTION OF THE PREFERRED EMBODIMENTS

It is to be understood that the figures and descriptions of the present invention have been simplified to illustrate elements that are relevant for a clear understanding of the present invention, while eliminating for the purpose of clarity, many other elements found in typical mechanical connectors. Those of ordinary skill in the art will recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art. Furthermore, the embodiments identified and illustrated herein are for exemplary purposes only, and are not meant to be exclusive or limited in their description of the present invention.

The present invention may generally be described as including a pre-mounted gasket on the face or fitting of a connector. The present invention provides for an improved and greatly simplified gasket installation process with a significantly reduced chance of contamination when used in a sterilized environment. This construction and attachment mechanism eliminates the operator of the device from having to locate a clean gasket in their facility. The gaskets may be sterilized separately or along with the fitting and entire connector system, which may remove the need for physically handling and positioning the gasket for proper sealing and compression.

Figure 1:
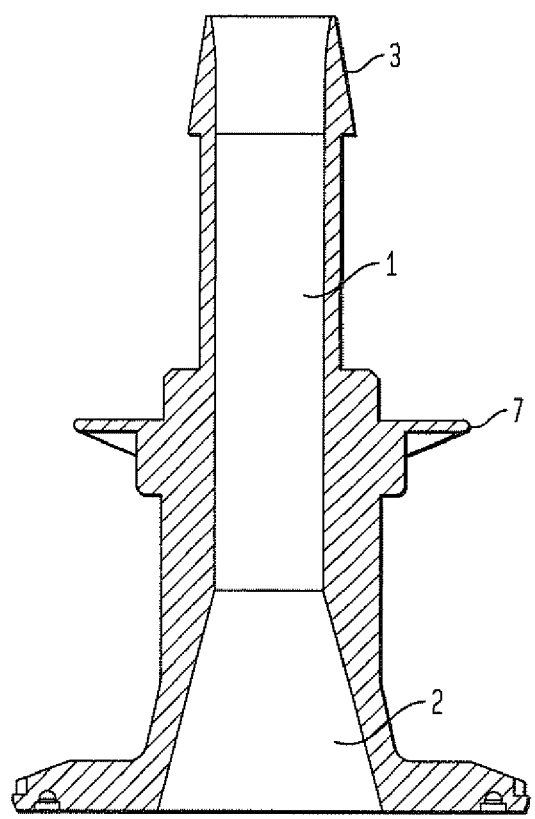
FIG. 1 is a cross sectional view of an exemplary connector, according to an aspect of the present invention.

According to an aspect of the present invention and as illustrated in FIG. 1) a connector is shown having a hollow barrel 1 and connector ends formed at opposite ends of barrel 1. A flange 7 is attached to and may be formed integrally with barrel 1 at a location on barrel 1 which is intermediate to the ends. A connector end 2, which may optionally have a larger diameter, is formed on an end of barrel 1 opposite connector end 3. As shown in FIGS. 2A-2G, this general connector configuration may take on many different embodiments, as the various types of tubing other connectors, or other machinery to which the present invention may connect to can vary.

According to an aspect of the present invention, the gaskets as described and illustrated herein throughout may be made of plastics, polymers, rubber, silicone, EPDM, steel, or any other material or combination of materials that may be manufactured sterile or subsequently sterilized by sterilization methods as understood by those skilled in the art.

According to an aspect of the present invention, the gasket may include one or more appendages located on the circumference or outer edge of the gasket. These appendages may be designed for engaging the face of the connector fitting for attachment. The appendages may be positioned at any point on the circumference of the gasket, provided that such positioning sufficiently provides for adequate attachment of the gasket to the face of the connector fitting. For example, the appendages and corresponding reciprocal cavities may be alternatively positioned on the inner circumference, the outer circumference, and anywhere in between.

Figure 3A:
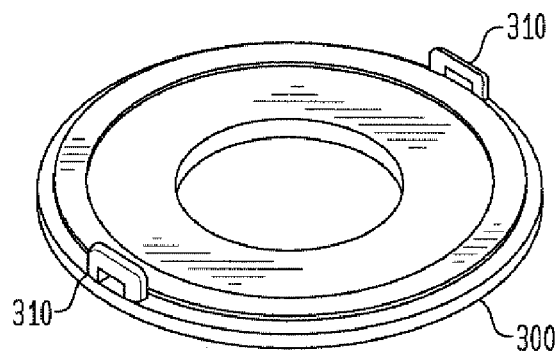
FIG. 3A is a perspective view of an exemplary gasket, according to an aspect of the present invention.
Figure 3B:
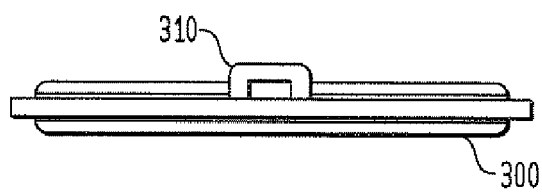
FIG. 3B is a side view of the exemplary gasket of FIG. 3A, according to an aspect of the present invention.
Figure 3C:
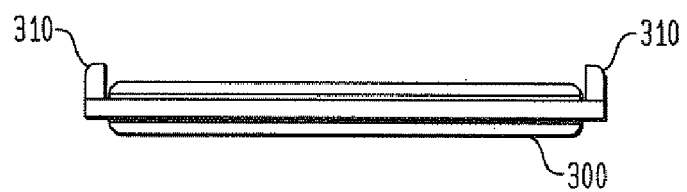
FIG. 3C is a front view of the exemplary gasket of FIG. 3B, turned 90°.
Figure 4A:
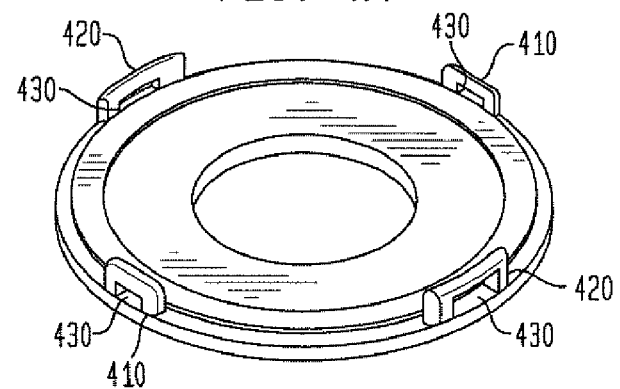
FIG. 4A is a perspective view of an exemplary gasket, according to an aspect of the present invention.
Figure 4B:
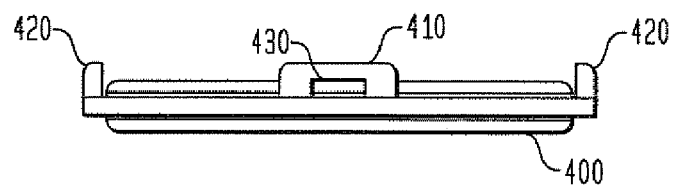
FIG. 4B is a side view of the exemplary gasket of FIG. 4A, according to an aspect of the present invention.
Figure 4C:
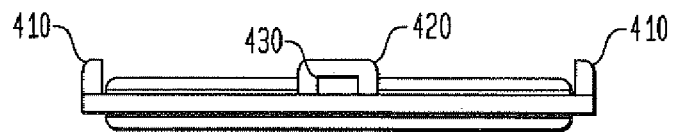
FIG. 4C is a front view of the exemplary gasket of FIG. 4B, turned 90°.

As shown in FIGS. 3A-3C, two appendages 310 of gasket 300 may be used, where each appendage is on the opposite side of the circumference, or approximately 180° from each other around the circumference of the connector fitting face. As shown in FIGS. 4A-4C, four appendages may be used, where each appendage is on an opposite side of another appendage, where each appendage is approximately 90° from each other around the circumference of the connector fitting face. In yet another example, three appendages may be used, where each appendage is equidistant from each other, or approximately 120° from each other around the circumference of the connector fitting face.

As explained previously, the gasket appendages may be designed for engaging the face of the connector fitting for attachment. The appendages may include any shape or structure that promotes the attachment of the gasket to the connector fitting. By non-limiting example only and referring again to FIGS. 4A-4C, the appendages are shaped as matching pairs, in that appendages 410 of gasket 400 have a first length, such as of approximately 0.3 inches, for example, while appendages 420 may have a second length, such as of approximately 0.484 inches, for example. Likewise, a cavity or whole 430 may be specifically sized and shaped for receiving a corresponding protrusion from the connector fitting to which the gasket must be attached.

Figure 5A:
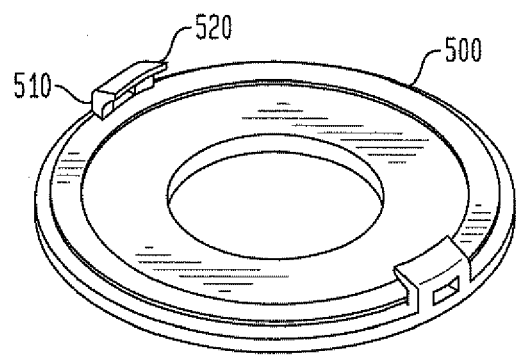
FIG. 5A is a perspective view of an exemplary gasket, according to an aspect of the present invention.
Figure 5B:
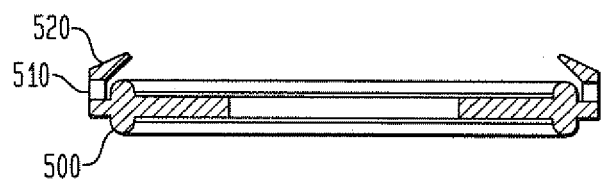
FIG. 5B is a cross sectional view of an exemplary gasket and appendage, according to an aspect of the present invention.
Figure 5C:
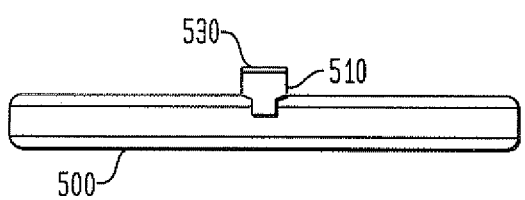
FIG. 5C is a side view of an exemplary gasket and appendage, according to an aspect of the present invention.
Figure 5D:
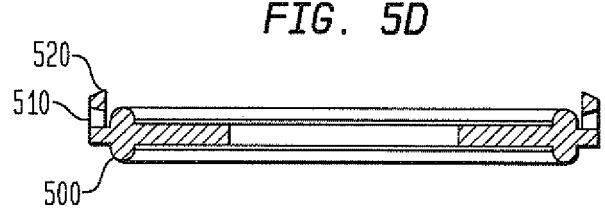
FIG. 5D is a cross sectional view of an exemplary gasket and appendage, according to an aspect of the present invention.

In another embodiment of the present invention, as shown in FIGS. 5A and 5B, appendage 510 of gasket 500 may include an overhanging portion 520 for engaging a groove or other reciprocal portion of the connector fitting. In yet other embodiments, such as that shown in FIG. 5C, for example, appendage 510 of gasket 500 may include a "T" shaped block 530 for engaging the connector fitting. The gasket appendages may alternatively be substantially u-shaped, v-shaped, a loop shape or any other shape suitable for engaging and interlocking with the cavities or reciprocal spaces positioned in the face of the connector fitting prior to compression. Further still, as shown in FIG. 5D, appendage 510 of gasket 500 may include a barbed portion 540 for engaging a reciprocal portion of the connector fitting. The gasket may also include one or more additional connecting mechanisms, such as a detent between the gasket and the connector fitting.

It should be appreciated that any shape or combination of shapes of one or more of the appendages may be used, provided the construction used promotes a reliable attachment of the gasket to the face of the connector fitting. In all cases, the gasket attachment may be temporary, meaning the gasket may be removed from the connector fitting, or it may alternatively be substantially permanent, meaning the gasket cannot be removed the connector fitting without at least a partial destruction of the gasket and/or connector fitting.

Likewise, the face of the connector fitting may have one or more cavities or reciprocal spaces sized and shaped for receiving and/or interlocking with the appendages of the gasket described herein. Any sort of protrusion, such as a shelf or hanger portion may be of any shape or contour, and may extend from within the cavity or from the outer edge of the circumference of the connector fitting face, provided such extension does not ultimately interfere with a clamp for connecting the two connector ends and gasket to create a seal suitable for a fluid connection. These cavities or reciprocal spaces, including any protrusions, may serve as "key slots" for engaging, receiving and/or interlocking the corresponding gasket appendages, and therefore creating a "lock and key" mechanism for either a temporary or substantially permanent attachment of the gasket to the fitting face.

Figure 6A:
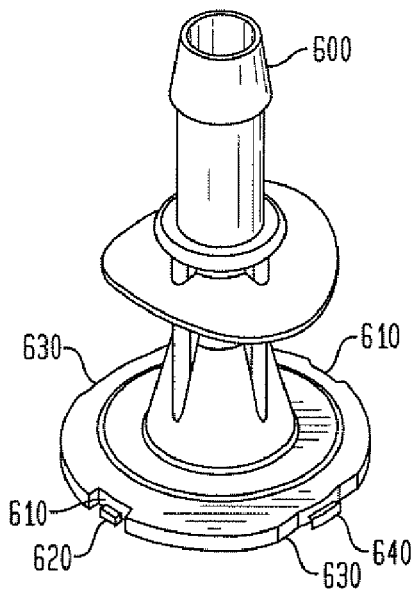
FIG. 6A is a perspective view of an exemplary connector, according to an aspect of the present invention.
Figure 6B:
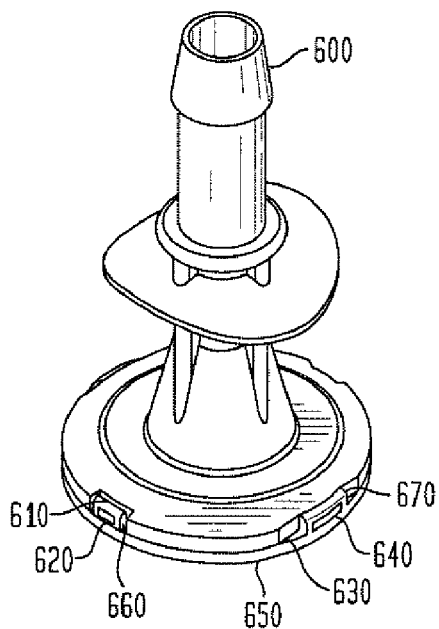
FIG. 6B is a perspective view of the exemplary gasket of FIG. 4A engaging the exemplary connector of FIG. 6A, according to an aspect of the present invention.
Figure 7A:
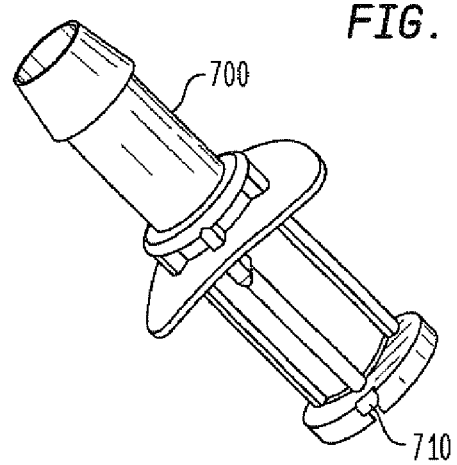
FIG. 7A is a perspective view of an exemplary connector, according to an aspect of the present invention.
Figure 7B:
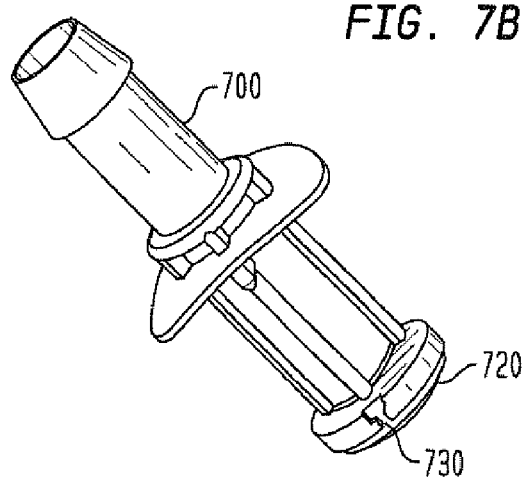
FIG. 7B is a perspective view of the exemplary gasket of FIG. 5C engaging the exemplary connector of FIG. 7A, according to an aspect of the present invention.

For example, as shown in FIG. 6A, connector fitting 600 may include a first pair of matching cavities 610, inside of which is a protrusion 620. Connector fitting 600 may also include a second pair of matching cavities 630 that are larger than cavities 610, such that cavities 630 reduce the radial distance of the outer edge of the connector fitting circumference. Likewise, cavities 630 may include their own protrusion 640. As shown in FIG. 6B, gasket 650 may engage connector fitting 600 for a temporary but secure attachment. As shown, the first gasket appendage pair 660 having a hole therein engages reciprocal connector fitting cavities 610, with protrusion 620 fitting within the hole of appendage 660. Likewise, the second gasket appendage pair 670, also having a hole therein, engages reciprocal connector fitting cavities 630, with corresponding protrusion 640 fitting within the hole of appendage 670. In another embodiment as shown in FIGS. 7A and 7B, connector fitting 700 may include matching "T" shaped cavities 710, for receiving corresponding "T" shaped appendages 730 of gasket 720. It should be appreciated that this connection mechanism may work for any gasket appendage and reciprocal cavity shapes as described herein and as understood by those skilled in the art.

The number of such cavities or reciprocal spaces should at least be equal to the number of gasket appendages. Additional cavities or reciprocal spaces may be present, provided such spaces do not interfere with the sealing of the fittings and gasket structure when compressed.

During manufacture of the fitting, the gasket appendages may be installed to the connector fitting face prior to sterilization and/or sealing of any surrounding pouch. Adhesives and/or various thermal methods, as understood by those skilled in the art, may also be used in conjunction with the attachment mechanism as described herein.

The present invention also includes a method of creating a connection between two connector fittings. For example, in no particular order, the method may include the steps of engaging some or all of the appendages of a gasket with a reciprocally shaped receiving component of the connector fitting, such that the gasket is at least temporarily secured to the end of the connector fitting, sterilizing the gasket and connector fitting, placing the end of a second connector fitting adjacent to the gasket attached to the first connector fitting, such that the gasket is between the ends of the two connector fittings, and clamping the two connector fitting ends and gasket such that the gasket is compressed to form a seal and thereby create a connection between the two connector fittings. The method may alternatively require that the gasket and first connector fitting are sterilized prior to securing the gasket to the first connector fitting, or may alternatively require that the gasket and first connector fitting are sterilized subsequent to securing the gasket to the first connector fitting.

Those of ordinary skill in the art will recognize that many modifications and variations of the present invention may be implemented without departing from the spirit or scope of the invention. Thus, it is intended that the present invention cover the modification and variations of this invention provided they come within the scope of the appended claims and their equivalents.

The invention claimed is:

1. A connector assembly comprising:
   a connector fitting having at least one receiving cavity in the face of the connector fitting, wherein the at least one cavity includes a protrusion;
   a gasket having at least one appendage;
   wherein the at least one appendage of the gasket engages the at least one receiving cavity, said receiving cavity is sized and shaped for receiving and interlocking with the at least one appendage of the gasket to at least temporarily secure attachment of the gasket to the connector fitting;
   wherein the at least one appendage includes a hole sized to receive the protrusion extending from said at least one receiving cavity when said gasket is attached to an end of said connector fitting;
   wherein ones of the at least one gasket appendages are of different sizes, and ones of the at least one receiving cavity are of different sizes; and
   wherein the attached gasket and connector fitting are connected to a second connector fitting via a clamp, such that the gasket compresses between the connector fittings to form a sealed fluid connection.

2. The connector assembly of claim 1, wherein the connector assembly is sterile.

3. The connector assembly of claim 1, wherein each one of the differently sized at least one receiving components are reciprocally matched to receive each one of the differently sized at least one gasket appendages.

4. The connector assembly of claim 1, wherein the at least one gasket appendage includes an overhanging portion.

5. The connector assembly of claim 1, wherein the at least one gasket appendage is "T"-shaped.

6. The connector assembly of claim 1, wherein the at least one gasket appendage includes a barbed portion.

* * * * *